United States Patent [19]

Hattori et al.

[11] 3,981,907

[45] Sept. 21, 1976

[54] METHOD OF PRODUCING HIGHLY UNSATURATED COMPOUNDS BY REACTING 1,3-CONJUGATED DIENE COMPOUNDS WITH DERIVATIVES OF DIMERS OF BUTADIENES AND PRODUCTS

[75] Inventors: Saburo Hattori; Yoshiharu Morita, both of Tokyo; Yoshio Ihashi, Kawasaki; Tadao Sato, Tokyo, all of Japan

[73] Assignee: Mitsubishi Chemical Industries Ltd., Japan

[22] Filed: Mar. 18, 1975

[21] Appl. No.: 559,563

Related U.S. Application Data

[63] Continuation-in-part of Ser. No. 109,553, Jan. 25, 1971, abandoned.

[30] Foreign Application Priority Data

| Jan. 28, 1970 | Japan | 45-7484 |
| Feb. 25, 1970 | Japan | 45-16092 |
| Feb. 25, 1970 | Japan | 45-16093 |
| Mar. 6, 1970 | Japan | 45-19136 |

[52] U.S. Cl............... 260/488 H; 260/476 R; 260/491; 260/497 A; 260/612 D; 260/614 AA; 260/642 R
[51] Int. Cl.$^2$............................ C07C 67/28
[58] Field of Search............ 260/488 H, 497 A, 491, 260/476 R, 632 R

[56] References Cited
UNITED STATES PATENTS

| 2,533,938 | 12/1950 | Jenner | 260/488 H |
| 3,407,224 | 10/1968 | Smutny | 260/476 R |
| 3,534,088 | 10/1970 | Bryant et al. | 260/497 A |
| 3,562,314 | 2/1971 | Shryne | 260/476 R |

OTHER PUBLICATIONS

March, Adv. Org. Chem.: Reactors, Mechn. & Structure, 1968, p. 603.
Alderson et al., J.A.C.S., 87, 1965, pp. 5638–5645.
Krauch et al., Name Reactions in Org. Chem., 1964, pp. 128–129.

*Primary Examiner*—Vivian Garner
*Attorney, Agent, or Firm*—Bierman & Bierman

[57] ABSTRACT

A 1,3-conjugated diene compound and a derivative of a butadiene dimer are subjected to an addition reaction over a rhodium compound. The 1,3-conjugated diene compound adds to the derivative in a molar ratio of 1:1. The derivative may be an ester, ether or alcohol. Said derivative is obtained either by reacting a carboxylic acid, an alcohol or a phenol with a butadiene over a palladium catalyst or by hydrolyzing the reaction product.

12 Claims, No Drawings

METHOD OF PRODUCING HIGHLY UNSATURATED COMPOUNDS BY REACTING 1,3-CONJUGATED DIENE COMPOUNDS WITH DERIVATIVES OF DIMERS OF BUTADIENES AND PRODUCTS

This is a continuation-in-part of United States application Ser. No. 109,553 Filed Jan. 25, 1971, now abandoned.

This invention relates to a method for the production of a substance resulting from the addition reaction between 1,3-conjugated diene compounds and derivatives of dimers of butadienes and to such substance. More particularly, the invention relates to a method for the production of a substance produced by addition reactions between 1,3-conjugated diene compounds and straight-chain dimers of butadienes, said dimers having a substituent group attached to the 1-or 3-position. As used in this specification "butadienes" means 1,3-butadiene and its homologues having a substituent alkyl group attached to the carbon atom at the 2-or 3-position, and the term "1,3-conjugated diene compounds" is applied to all those compounds which contain 1,3-conjugated diene bonds, e.g., said butadienes and 1,3,7-octatriene.

Methods for the production of dimers of butadienes and derivatives thereof are known. For example, it is known in the prior art to produce straight-chain octatrienes from butadienes using palladium acetate and triphenylphosphine as a catalyst. It is also known to react butadienes in the presence of said catalysts with active hydrogen containing compounds such as alcohols, phenols, carboxylic acids, and primary or secondary amines to produce derivatives of dimers of butadienes which contain a structure such that an active hydrogen containing compound adds to the carbon atom at the 1-or 3-position of a straight-chain dimer of butadienes. However, the prior art is silent with regard to a method for the selective production of derivatives of oligomers of butadienes which are trimers or tetramers. Since these compounds comprise at least 12 carbon atoms, having at least three carbon-carbon double bonds, they are widely useful as raw materials in the manufacture of surfactants.

An object of the instant invention is to provide a method for producing a substance by an addition reaction between a compound having 1,3-conjugated diene bonds and a compound containing a structure such that a hydroxy, alkoxy, aryloxy, or acyloxy group is attached to the carbon atom at the 1-or 3-position of a straight-chain dimer of butadienes.

Another object of the invention is to provide a method for the production of derivatives of oligomers or cooligomers of butadienes which are trimers or tetramers.

A further object of the invention is to provide a method for producing alcohols, ethers or esters having an alkatrienyl group which corresponds to trimers or co-trimers of butadienes in which butadienes react with compounds which contain a structure such that a hydroxy, alkoxy, aryloxy, or acyloxy group is attached to the carbon atom at the 1-or 3-position of a straight-chain dimer of butadienes.

A still further object of the invention is to provide a method for producing alcohols, ethers or esters having an alkatetraenyl group which corresponds to tetramers or co-tetramers of butadienes in which a straight-chain dimer of butadienes reacts with a compound which contains a structure such that a hydroxy-, alkoxy-, aryloxy- or acyloxy group is attached to the carbon atom at the 1-or 3-position of said dimer.

Still another object of the invention is to provide novel substances produced by the aforesaid methods.

These and other objects and features of the invention will become apparent as the description progresses.

According to the invention, a 1,3-conjugated diene compound, represented by the formula

(1)

in which the $R_1$ groups may differ from one another, $R_1$ is hydrogen or alkyl and $R_2$ is hydrogen, alkyl, or alkenyl, is reacted with an alkadienyl group containing compound, represented by the formula

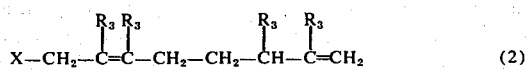

(2)

or

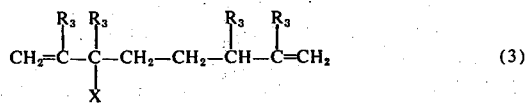

(3)

in which the $R_3$ groups may differ from one another, $R_3$ is hydrogen or alkyl and X is hydroxy-, alkoxy-, aryloxy-, over a rhodium compound, to produce a compound which possesses at least 12 carbon atoms and at least 3 carbon-carbon double bonds and which has a structure in which the 1,3-conjugated diene compound represented by the formula (1) is added to a compound represented by the formula (2) or (3).

The present invention will now be illustrated in greater detail.

The 1,3-conjugated diene compound having the formula (1) used as the starting material in the method of the present invention, may be butadienes as for example 1,3-butadiene, isoprene, or 2,3-dimethyl butadiene. Additionally it may be piperylene or the like in which the carbon atom at the 4-position of 1,3-butadiene has a substituent alkyl group. Further, it may be 1,3,7-octatriene, 2,6-dimethyl-1,3,7-octatriene, 2,7-dimethyl-1,3,7-octatriene or the like in which the carbon atom at the 4-position of butadiene has a substituent alkenyl group.

Preferred 1,3-conjugated diene compounds are 1,3-butadiene, isoprene and 1,3,7-octatriene, 1,3-butadiene is most preferred.

The term "alkadienyl group containing compounds" indicated by the formula (2) or (3) is applied to esters, ethers and alcohols which are derivatives of straight-chain dimers of butadienes. Esters and ethers, among other alkadienyl group containing compounds, may readily be produced by the conventional method of reacting butadienes with carboxylic acids, alcohols or phenols. For example, the reaction of 1,3-butadiene with a carboxylic acid, such as acetic acid, propionic acid, n-butyric acid, or benzoic acid, in the presence of a catalyst comprising palladium acetate and triphenylphosphine gives 1-acyloxyl-2,7-octadiene and/or 3-acyloxy-1,7-octadiene. The employment of alcohols such as methanol, ethanol, allyl alcohol, or phenols such as phenol or cresol, in place of the carboxylic acid, gives 2,7-octadiene and/or 1,7-octadiene having an alkoxy group or phenoxy group attached at the 1-or 3-position. Further, the employment of isoprene in place of 1,3-butadiene in these reactions, gives the carbon chain of a 1,3-conjugated diene compound. The former substance will hereinafter be referred to as "normal type-compound" and the latter as "iso type-compound". For example, the above-mentioned reaction occurs between 1,3-butadiene and 1-acetoxy-2,7-octadiene as follows:

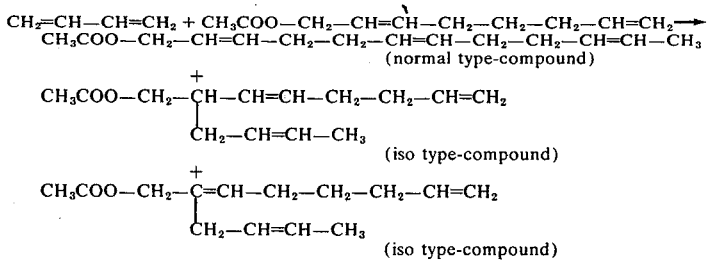

same ester or ether except that it has two methyl groups as side-chains. In this case, the two methyl groups are linked to carbon atoms at the 2-and 6-positions or at the 2-and 7-positions. The employment of butadienes other than 1,3-butadiene and isoprene also gives esters or ethers corresponding to those produced from 1,3-butadiene. Further, alkadienyl alcohol is produced by hydrolysing acyloxyalkadienes manufactured in the manner mentioned. Preferred examples of such compounds having an alkadienyl group thus produced include 1-acetoxy-2, 7-octadiene, 1-methoxy-2,7-octadiene, 1-phenoxy-2,7-octadiene, 1-hydroxy-2,7-octadiene, 3-acetoxy-1,7-octadiene, 3-methoxy-1,7-octadiene, 3-phenoxy-1,7-octadiene, and 3-hydroxy-1,7-octadiene which are derivatives of the dimer of 1,3 butadiene. Derivatives of the dimer of isoprene which correspond to these are also preferred. Among them 1-acetoxy-2,7-octadiene is most preferred.

The method of the invention employs rhodium compounds as the catalyst. The catalyst may be an inorganic acid salt, an organic acid salt, or an organic complex, of rhodium. Examples of such rhodium compounds include inorganic acid salts of rhodium such as rhodium chloride, rodium bromide and rhodium nitrate, carboxylic acid salts of rodium such as rhodium acetate and rhodium propionate, chelate compounds of rhodium such as rhodium acetylacetonate; $\pi$-allyl-type complexes of rhodium such as $\pi$-allyl-rhodium chloride; and other rhodium complexes such as tetrakis (ethylene) dichloro dirhodium [Rh(C$_2$H$_4$)2 Cl] 2, bis (cycloocta-1,5-diene) dichloro dirhodium [Rh (C$_8$H$_{12}$)Cl]$_2$. Rhodium chloride, RhCl$_3$.3H$_2$O is especially preferred. These rhodium compounds may be added directly to the reaction system. However, the use of an alcoholic solution of the rhodium compound facilitates the reaction and brings about better results. To this end primary alcohols such as methanol, ethanol and isopropanol are preferred.

According to the invention, the reaction between a 1,3-conjugated diene compound represented by the formula (1) and an alkadienyl compound having a substituent group at the 1-position, represented by the formula (2) in the presence of a rhodium compound mainly gives rise to a straight-chain substance having a structure in which the carbon atom at the 8-position of 1-substituted alkadiene is linked to the terminal carbon atom of the carbon chain of a 1,3-conjugated diene compound and a substance having a structure in which the carbon atom at the 2-position of 1-substituted alkadiene is linked to the terminal carbon atom of the Further, presumably the employment of an alkadienyl compound represented by the formula (3) as the alkadienyl group containing compound which has a substituent group at the 3-position mainly gives a substance which has a structure such that the carbon atom at the 7-position of a 3-substituted alkadiene is linked to the carbon atom at the 1-position of a 1,3-conjugated diene compound, and possibly a substance which has a structure such that the carbon atom at the 1-or 2-position of a 3-substituted alkadiene is linked to the carbon atom at the 1-position of a 1,3-conjugated diene compound.

Since normally the reaction of an n-α-olefin with a conjugated diene results in the formation of a linkage between the carbon atom at the 2-position of the n-α-olefin and the conjugated diene, we were surprised to discover that in the case of the 1-substituted-n-octadiene or 3-substituted-n-octadiene employed in the method of the invention a conjugated diene was linked to the terminal carbon atoms of the chain or to the carbon atoms constituting inner carbon-carbon double bonds.

The production of the said substance resulting from the reaction of a 1,3-conjugated diene compound with a derivative of dimers of butadienes may be effected according to various modes. For example, a 1,3-conjugated diene compound such as 1,3-butadiene, an alkadienyl group containing compound such as 1-acetoxy-2,7-octadiene and a catalyst such as rhodium chloride are charged into a reactor, such as an autoclave, and heated at a temperature in the range of 50°–250°C, preferably in the range of 70°–200°C, under stirring for a period of from several ten minutes to ten and several hours and preferably under an inert atmosphere.

The 1,3-conjugated diene compound and the alkadienyl group containing compound are charged into the reactor normally in the ratio of 0.1–10 moles of the former to 1 mole of the latter. The rhodium compound catalyst is employed in an amount of from $10^{-4} - 10^{-2}$ moles to 1 mole of the alkadienyl group containing compound.

In effecting the reaction, the reactant compounds may be used as such. Alternatively, they may be dissolved in a solvent and employed in solution form. Examples of said solvent include alcohols such as ethanol; organic acids such as acetic acid; hydrocarbons such as benzene; ketones such as acetone; and other various types of solvents that are inert to the reaction, such as methylene dichloride, tetrahydrofuran, and acetonitrile. Amide type-aprotic polar solvents such as dimethylformamide, dimethylacetamide, pyrrolidone, N-methyl pyrrolidone, and tetramethyl urea may also be employed. Further, in order to obtain better reaction results, a polymerization inhibitor such as t-butyl-catechol and phenothiazine or a titanium compound such as tetrabutoxy titanium tetrachloride may be added. When a 1-substituted-alkadiene represented by the formula (1) is employed as the alkadienyl group containing compound, the addition of a trivalent phosphorus compound such as triphenylphosphine, tri-n-butylphosphine, tri-iso-propylphosphine, tricyclohexylphosphine, phenyldichlorophosphine, phosphorus trichloride, and triphenylphosphite to the reaction system brings about an increase in the normal type-compound-/iso type-compound ratio, in other words, production of the normal type compound increases.

The novel substances produced according to the method of the invention are extensively useful for the production of intermediates in organic synthesis. For example, hydrolysis of the esters gives unsaturated higher alcohols. Hydrogenation hydrolysis gives saturated higher alcohols. These substances may be converted via other reactions such as sulfonation to surfactants, or they may be used without further reaction. Moreover, our novel substances are directly used as raw materials from which various resinous materials such as synthetic drying oils or modified alkyd resins are produced.

Some preferred examples of the invention will now be described. They are offered only for the purpose of illustrating the invention and not in limitation thereof.

EXAMPLE 1

A solution of 0.13g (0.5 mmol) $RhCl_3 \cdot 3H_2O$ in 0.92 g (20 mmol) ethanol and 33.6 g (0.2 mol) 1-acetoxy 2,7-octadiene were charged into a 100 c.c. autoclave. 21.6 g (0.4 mol) 1,3-butadiene were added thereto and heated therewith to 110°C. The reaction was carried out for 4 hours. Upon completion of the reaction, the autoclave was purged of unreacted 1,3-butadiene. 44.9 g of reaction solution were obtained. The reaction solution was distilled and analyzed by gas-chromatography. It was found to be composed chiefly of two components, an A-component having a boiling point of 77°–86°C/2mmHg and a B- component having a boiling point of 96°–101°C/2mmHg.

Infrared-ray analysis of the B-component showed the absorption of C=O of the acetoxy group at 1730 cm$^{-1}$, and the absorption of the ether bond at 1,220 cm$^{-1}$, no absorption indicating the presence of a terminal vinyl group, and an absorption indicating the presence of inner olefin. The infrared ray spectrum of the B-component after hydrogenation and subsequent hydrolysis was identical with that of n-1-dodecanol. From this it was inferred that the B-component was a straight-chain compound having a terminal acetoxy group. Mass analysis of the B-component indicated absorptions at m/e 43($CH_3CO$), 61($CH_3(CO)OH_2$), 113($CH_3(CO)OCHO_2CH=CHCH_2$), 167($CH_3(CO)OCH_2CH=CHCH_2CH_2CH=CHCH_2$), and 162($CHCH=CHCH_2CH_2CH=CHCH_2CH_2CH=CHCH_3$). In view of the fact that the infrared-ray analysis showed no terminal vinyl, the B-component was thought to have a structure represented by the formula

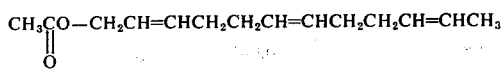

Further analysis of the B-component by NMR (Nuclear Magnetic Resonance) using TMS as a standard indicated absorptions at δ1.6 (terminal methyl, $CH_3$-), δ1.9 (methyl of acetoxy group, $CH_3(CO)O$—), δ2.1 (methylene,—$CH_2$—), δ4.45 (doublet; methylene linked to acetoxy group, $CH_3(CO)O$—$CH_2$—CH), and δ5.4 (vinylic hydrogen, =CH—). From these facts, it was concluded that the B-component was a compound represented by the above mentioned formula, that is, 1-acetoxy-2,6,10-dodecatriene (normal type-compound). Gas-chromatographic analysis indicated that the B-component was a mixture of cis-,trans-isomers of 1-acetoxy 2,6,10-dodecatriene.

Regarding the A-component, a mass analysis after hydrogenation indicated no absorption of M/e 87 ($CH_3(CO)OCH_2CH_2$), and showed instead an absorption at 73 ($CH_3(CO)OCH_2$) and at 143 ($CH_3(CO)OCH_2CH_2CH_2CH_2CH_2CH_3$) This indicated that the hydrogenated A-component contained a butyl group as side-chain. Further analysis by means of NMR indicated absorptions at δ0.9 (terminal methyl, $CH_3$—), δ1.3 (methylene, —$CH_2$—), δ1.96 (methyl of acetoxy group, $CH_3$ (CO)O—), and δ3.9 (doublet; methylene linked to acetoxy group, $CH_3(CO)O$—$CH_2$—CH—). The fact that the absorption at δ3.9 was doublet indicates that only one hydrogen atom was linked to the carbon atom linked to the acetoxy methyl group, and butyl group linked to said carbon atom as a side-chain. From these facts it was deduced that the structure of the hydrogenated A- component contained an acetoxy group at the 1-position and a butyl group linked at the 2-position.

The A-component was immediately further separated into two components, A-1 and A-2, by means of a gaschromatographic analysis. Mass analysis of the A-1 component showed absorptions at M/e 167 ($CH_3(CO)OCH_2CHCH=CHCH_2CH_2CH=CH_2$) and at 125 ($CH_3(CO)OCH_2CHCH=CHCH$). An NMR analysis showed absorptions at δ1.6 (terminal methyl, $CH_3$—), δ1.9 (methyl of acetoxy group, $CH_3(CO)O$—), δ2.1 (methylene, —$CH_2$—), and δ3.9 (doublet; methylene linked to acetoxy group, $CH_3(CO)O$—$CH_2$—CH). Thus, the A-1 component was believed to be 1-acetoxy-2-(2-butenyl)-3,7-octadiene (iso type-compound) represented by the formula

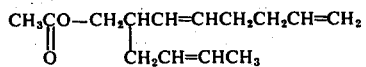

Mass analysis of the A-2 component showed an absorption at M/e 180 ($CH_3(CO)OCH_2C(CH_2CH=CHCH_3)$ $CHCH_2CH$) no absorption at M/e 167 and the elimination of butenyl group This indicated that there were double bonds at carbon atoms to which a side-chain was attached. Further a NMR analysis showed absorptions at δ1.6 (terminal methyl, $CH_3$—), δ1.9 (methyl of acetoxy group, $CH_3(CO)O$—), δ2.1 (methylene, —$CH_2$—), δ2.6 (methylene between two adjacent double bonds, =C-$CH_2$-C=), and δ4.5 (singlet; methylene linked to acetoxy group $CH_3(CO)O$—$CH_2$—C=). In view of the fact that the absorption at δ4.5 was singlet, it was inferred that no hydrogen was attached to the carbon atom linked to the acetoxy methyl group. In view of the absorption at δ2.6, it was inferred that the A-2 component was 1-acetoxy-2(2-butenyl)-2,7-octadiene (iso type-compound) represented by the following formula:

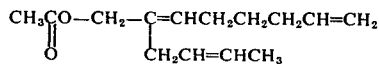

The reaction solution was composed of 21.0 g of 1-acetoxy-2,6,10-dodecatriene, 14.4 g of 1-acetoxy-2(2-butenyl)-3,7-octadiene and 1-acetoxy-2(2-butenyl)-2,7-octadiene, and 6.1 g of unreacted 1-acetoxy-2,7-octadiene. This indicates an 81.8% conversion of 1-acetoxy-2,7-octadiene, a 97.6% selectivity of reaction products and a 1.46 ratio of normal type-compound to iso type-compound.

EXAMPLE 2

The same process as described in example 1 was followed for reacting 1,3-butadiene with 1-acetoxy-2,7-octadiene over 0.13 g $RhCl_3 \cdot 3H_2O$ in a solution of 0.92 g ethanol and in the presence of various additives. The reaction conditions and the reaction results are listed in the following table 1.

Table 1

| Run | 1 | 2 | 3 | 4 |
|---|---|---|---|---|
| 1,3-butadiene, mol | 0.4 | 0.1 | 0.2 | 0.2 |
| 1-acetoxy-2,7-octadiene, mol | 0.2 | 0.2 | 0.2 | 0.2 |
| Additive Kind | 1-butyl-catechol | '' | '' | '' |
| mg | 20 | 20 | 20 | 20 |
| Reaction temp., °C | 110 | 120 | 80 | 140 |
| Reaction period, hr | 2 | 5 | 5 | 0.25 |
| *1 Conversion, % | 87.2 | 31.0 | 54.7 | 78.3 |
| *2 Selectivity, % | 72.7 | 78.0 | 100 | 83.7 |
| *3 n/iso ratio | 1.77 | 2.26 | 1.50 | 1.38 |

| Run | 5 | 6 | 7 |
|---|---|---|---|
| 1,3-butadiene, mol | 0.4 | 0.2 | 0.4 |
| 1-acetoxy-2,7-octadiene, mol | 0.2 | 0.2 | 0.2 |
| Additive Kind | $Ti(OC_4H_9)_4$ | $TiCl_4$ | phenothiazine |
| mg | 34 | 190 | 34 |
| Reaction temp., °C | 110 | 120 | 110 |
| Reaction period, hr | 1 | 1 | 1 |
| *1 Conversion, % | 84.7 | 42.3 | 66.5 |
| *2 Selectivity, % | 81.3 | 100 | 72.0 |
| *3 n/iso ratio | 1.48 | 1.56 | 1.79 |

Table 1-continued

Note:
*1 Conversion of 1-acetoxy-2,7-octadiene
*2 Selectivity of reaction products comprising normal type-compound and iso type-compound
*3 Ratio of normal type-compound produced to iso type-compound produced

EXAMPLE 3

The same process as described in example 1 was followed for reacting 5.4 g (0.1 mol) 1,3-butadiene with 16.8 g (0.1 mol) 1-acetoxy-2,7-octadiene, in the presence of a solution of 0.065 g (0.25 mmol) $RhCl_3 \cdot 3H_2O$ in 0.46 g (10 mmol) ethanol. The 1,3-butadiene and the 1-acetoxy -2,7 octadiene were used in solution form. The solvent employed to effect said solution was varied. The following table 2 indicates the reaction conditions and the reaction results. The respective amounts of the catalyst, 1,3-butadiene and 1-acetoxy-2,7 octadiene employed in run 1 were twice the amount employed in each of the other runs.

Table 2

| Run | Solvent Kind | g | Reaction temp., °C | Reaction period, hr |
|---|---|---|---|---|
| 1 | acetic acid | 12 | 120 | 1,5 |
| 2 | acetone | 16.8 | 120 | 2 |
| 3 | '' | 16.8 | 110 | 4 |
| 4 | benzene | 16.8 | 120 | 2 |
| 5 | methylene bichloride | 16.8 | 120 | 2 |
| 6 | tetrahydrofuran | 16.8 | 120 | 2 |
| 7 | acetonitrile | 16.8 | 120 | 2 |
| 8 | dimethyl formamide | 16.8 | 120 | 3 |
| 9 | dimethyl acetoamide | 16.8 | 120 | 3 |

| Run | Conversion, % | Selectivity, % | n/iso ratio |
|---|---|---|---|
| 1 | 83.7 | 96.0 | 1.44 |
| 2 | 57.1 | 98.3 | 2.35 |
| 3 | 23.2 | 100 | 1.52 |
| 4 | 88.7 | 64.7 | 1.84 |
| 5 | 83.0 | 74.4 | 1.63 |
| 6 | 84.3 | 92.8 | 1.37 |
| 7 | 69.0 | 80.4 | 1.66 |
| 8 | 35.4 | 88.7 | 2.61 |
| 9 | 39.4 | 96.7 | 2.94 |

EXAMPLE 4

The same process as described in example 1 was followed. Ethanol was employed as the solvent and a phosphorus compound was added to the reaction system. The phosphorus compound was varied. The reaction conditions and the reaction results are listed in table 3.

Table 3

| Run | 1 | 2 | 3 | 4 |
|---|---|---|---|---|
| 1,3-butadiene, mol | 0.1 | 0.1 | 0.1 | 0.2 |
| 1-acetoxy-2,7-octadiene, mol | 0.1 | 0.1 | 0.1 | 0.2 |
| Catalyst $RhCl_3 \cdot 3H_2O$, g | 0.065 | 0.065 | 0.065 | 0.052 |
| Phosphorus |  |  |  |  |

Table 3-continued

| Run | 1 | 2 | 3 | 4 |
|---|---|---|---|---|
| compound, Kind | P(n-C₄H₉)₃ | P(-O-⬡)₃ | P(⬡(H))₃ | P(⬡)₃ |
| mmol | 0.18 | 0.25 | 0.27 | 0.2 |
| Solvent Ethanol, g | 16.8 | 16.8 | 16.8 | 0.92 |
| Reaction temp., °C | 120 | 120 | 120 | 120 |
| Reaction period, hr | 8 | 6 | 3 | 6.5 |
| Conversion, % | 51.7 | 28.3 | 57.8 | 51.7 |
| Selectivity, % | 71.4 | 82.3 | 79.3 | 100 |
| n/iso ratio | 3.03 | 10.7 | 2.43 | 2.44 |

As shown by Table 3 the addition of phosphorus compounds to the reaction system resulted in increased n/iso ratios.

EXAMPLE 5

The same process as described in example 1 was followed to effect the reaction. However, instead of using $RhCl_3 \cdot 3H_2O$ as the catalyst, other rhodium compounds were employed. The reaction conditions and the reaction results are shown in Table 4.

Table 4

| Run | 1 | 2 | 3 |
|---|---|---|---|
| 1,3-butadiene, mol | 0.1 | 0.1 | 0.2 |
| 1-acetoxy-2,7-octadiene, mol | 0.1 | 0.1 | 0.1 |
| Catalyst Kind | RhBr₃ | Rh(NO₃)₃ | [Rh(OCOCH₃)₂]₂ |
| mmol | 0.25 | 0.5 | 0.2 |
| Solvent Kind | ethanol | " | " |
| g | 16.8 | 16.8 | 16.8 |
| Reaction temp., °C | 120 | 120 | 120 |
| Reaction period, hr | 6 | 3 | 3 |
| Conversion, % | 53.8 | 30.8 | 15 |
| Selectivity, % | 66.8 | 54.2 | 30 |

| Run | 4 | 5 | 6 |
|---|---|---|---|
| 1,3-butadiene, mol | 0.2 | 0.2 | 0.2 |
| 1-acetoxy-2,7-octadiene, mol | 0.1 | 0.1 | 0.1 |
| Catalyst Kind | [Rh(C₂H₄)₂Cl]₂ | " | [Rh⬡Cl]₂ |
| mmol | 0.025 | 0.025 | 0.05 |
| Solvent Kind | acetic acid | trichloromethane | — |
| g | 1.0 | 0.8 | — |
| Reaction temp., °C | 120 | 120 | 120 |
| Reaction period, hr | 3 | 3 | 5 |
| Conversion, % | 10 | 8 | 5 |
| Selectivity, % | ca. 100 | ca. 100 | ca. 100 |

EXAMPLE 6

A solution of 0.13 g (0.5 mmol) $RhCl_3 \cdot 3H_2O$ in 0.92 g (20 mmol) ethanol was charged together with 16.8 g (0.1 mol) 1-acetoxy-2,7-octadiene into a 100 c.c. autoclave. 13.6 g (0.2 mol) isoprene were added thereto, and heated therewith at 120°C. The reaction was carried out for 3 hours. 30.2g of reaction solution were obtained. Unreacted isoprene was distilled off from the reaction solution. The reaction solution was then found to be composed of 8.2 g acetoxytridecatrienes and 8.3 g 1-acetoxy-2,7-octadiene. Similiarly to the acetoxydodecatriene produced in preceding examples, these reaction products consisted of normal type-compounds and iso type-compounds in a 2.45 n/iso ratio.

EXAMPLE 7

The same process as described in example 1 was followed for the reaction however 1-methoxy-2,7-octadiene was substituted for 1-acetoxy-2,7-octadiene. A solution of 0.13 g (0.5 mmol) $RhCl_3 \cdot 3H_2O$ in 0.92 g ethanol was charged together with 28.0 g (0.2 mol) 1-methoxy-2,7-octadiene into a 100 c.c. autoclave. About 11 g (0.2 mol) 1,3-butadiene were added thereto and heated therewith at 120°C. The reaction was carried out for 1.5 hours. Upon completion of the reaction, the autoclave was purged of unreacted 1,3-butadiene to give 36.2 g of reaction solution. The reaction solution was distilled. 13.2 g of unreacted 1-methoxy-2,7-octadiene and 15.8 g of the fraction collected at fractionation temperature of 55°–64°C/0.012 mm Hg. were obtained. Analyses by means of gas-chromatography and mass spectrum showed that this fraction was an isomer mixture comprising 1-methoxy-2,6,10-dodecatrienes, 1-methoxy-2-(2-butenyl)-3,7-octadiene and 1-methoxy-2-(2-butenyl)-2,7-octadiene in a 1.5 n/iso ratio. Accordingly, the conversion of 1-methoxy-2,7-octadiene was calculated to be 53%. The selectivity of methoxy dodecatriene was 77% for the sum of normal type- and iso type-compounds.

EXAMPLE 8

The same process as described in example 7 was followed. However, 1-phenoxy-2,7-octadiene was substituted for 1-methoxy-2,7-octadiene.

A solution of 0.13 g $RhCl_3 \cdot 3H_2O$ in 1.84 g ethanol and 20.2 g (0.1 mol) 1-phenoxy-2,7-octadiene were charged into a 100 c.c. autoclave. About 11 g 1,3-butadiene were added thereto, and heated therewith at 120°C. The reaction was carried out for 2.5 hours. Upon completion of the reaction, unreacted 1,3-butadiene was purged from the autoclave, leaving 30.2 g of reaction solution. The reaction solution was washed with water, dried with sodium sulphate, and filtered through activated charcoal. The filtrate was distilled. 3.5 g of unreacted 1-phenoxy-2,7-octadiene and 9.1 g of the fraction collected at the fractionation temperature of 113–143°C/1.5 mm Hg. were obtained. This fraction was analyzed by the same means as described in example 7. It was found to be an isomer mixture comprising 1-phenoxy-2,6,10-dodecatriene, 1-phenoxy-2(2-butenyl)-3,7-octadiene and 1-phenoxy-2-(2-butenyl)-2,7-octadiene, in a 1.0 n/iso ratio. The conversion of 1-phenoxy-2,7-octadiene was 83%, and the selectivity of phenoxy dodecatriene was 45%.

EXAMPLE 9

The same process as described in example 7 was followed to effect the reaction, however, 1-hydroxy-2,7-octadiene was substituted for 1-methoxy-2,7-octadiene.

A solution of 0.065 g $RhCl_3·3H_2O$ in 0.46 g ethanol, 12.6 g benzene and 12.6 g (0.1 mol) 1-hydroxy-2,7-octadiene were charged into a 100 c.c. autoclave. About 6 g (0.11 mol) 1,3-butadiene were added thereto, and heated therewith at 120°C. The reaction was conducted for 7 hours. Upon completion of the reaction, unreacted 1,3-butadiene was purged from the autoclave, and the reaction solution was distilled. 2.5 g of unreacted 1-hydroxy-2,7-octadiene and 9.2 g of the fraction collected at the fractionation temperature of 82–91°C/1 mm Hg were obtained. An analysis was conducted as described in example 7. The results indicated that the fraction was an isomer mixture comprising 1-hydroxy-2,6,10-dodecatriene, 1-hydroxy-2-(2-butenyl)-2,7-octadiene, and 1-hydroxy-2(2-butenyl)-3,7-octadiene in a 4.0 n/iso ratio. The conversion of 1-hydroxy-2,7-octadiene was 80% and the selectivity of hydroxydodecatrienes was 64%.

EXAMPLE 10

In this example the reaction was effected as described in example 1, however 3-acetoxy-1,7-octadiene was employed in place of the 1-acetoxy-2,7-octadiene.

A solution of 0.13 g $RhCl_3·3H_2O$ in 0.92 g ethanol and 33.6 g (0.2 mol) 3-acetoxy-1,7-octadiene were charged into a 100 c.c. autoclave. 10.8 g (0.2 mol) 1,3-butadiene were added thereto, and heated therewith at 110°C. The reaction was carried out for 3 hours. Upon completion of the reaction the unreacted 1,3-butadiene was purged from the autoclave, leaving 43.7 g of reaction solution. The reaction solution was distilled. 19.6 g of unreacted 3-acetoxy-1,7-octadiene and 11.6 g of the fraction collected at fractionation temperatures 67°–79°C/0.005 mm Hg were obtained. Analysis by means of gas-chromatography and mass spectrum indicated that the fraction was acetoxy-dodecatriene. The distillation residue was a mixture of polymer and a tarry substance. The conversion of 3-acetoxy-1,7-octadiene was 41.8%. The selectivity of acetoxydodecatriene was 62.3%.

EXAMPLE 11

The same process as described in example 10 was followed, however the solvent was varied. The reaction conditions and the reaction results are listed in the following Table 5.

Table 5.

| Run | 1 | 2 | 3 |
|---|---|---|---|
| 1,3-butadiene, mol | 0.2 | 0.2 | 0.2 |
| 3-acetoxy-1,7-octadiene, mol | 0.1 | 0.1 | 0.1 |
| $RhCl_3·3H_2O$, mol | 0.5 | 0.5 | 0.5 |
| Solvent Kind | Ethanol / Benzene | Ethanol / Methylene bichloride | Acetone |
| g | 0.92 / 16.8 | 0.92 / 16.8 | 16.8 |
| Reaction temp., °C | 110 | 110 | 120 |
| Reaction period, hr | 3 | 3 | 3 |
| Conversion, % | 46.8 | 41.5 | 32.0 |
| Selectivity, % | 59.3 | 42.2 | 80.8 |

EXAMPLE 12

The same process as described in example 1 was followed, however 1,3,7-n-octatriene was substituted for 1,3-butadiene. A solution of 0.13 g (0.5 mmol) $RhCl_3·3H_2O$ in 0.92 g ethanol was charged along with 16.8 g (0.1 mol) 1-acetoxy-2,7-octadiene into a 100 c.c. autoclave, 10.8 g. (0.1 mol) 1,3,7-n-octatriene were added thereto, and heated therewith at a temperature of 105°–115°C. The reaction was carried out for 6 hours. The reaction solution was distilled. 7.2g of unreacted 1-acetoxy-2,7-octadiene and 6.8 g of the fraction collected at the fractionation temperature of 133°–145°C/1 mm Hg. were obtained. This fraction was analyzed by means of gas-chromatography and mass spectrum. It was found to be a mixture of isomers of acetoxy-hexadecatetraene.

EXAMPLE 13

The same process as described in example 12 was followed for the reaction, however, 3-acetoxy-1,7-octadiene was substituted for 1-acetoxy-2,7-octadiene. The reaction was carried out for 8 hours. Gas-chromatographic analysis of the reaction solution indicated the production of a $C_{16}$ tetraene having acetoxy group at about 6% yield.

EXAMPLE 14

The following experiments show that the products of the present invention are useful for producing sufactants.
A. Preparation of Surfactant
1. Preparation of Acetoxydodecatrienes. According to the method of Example 1 butadiene was reacted with 1-acetoxy-2,7-octadiene and the reaction solution was distilled to obtain a fraction boiling at 77°–86°C/2 mm Hg (a mixture of 2-butenyl- octadienyl acetates hereinafter abbreviated as iso-ADT) and a fraction boiling at 96–101°C/2 mmHg (1-acetoxydodecatriene, hereinafter abbreviated as n-ADT). Iso-ADT was further distilled and a fraction boiling at 128°–130°C/10 mm Hg was obtained as a starting material.
2. Methanolysis and Hydrogenation of Acetoxydodecatrienes. 5mmol of caustic soda was dissolved in 1.2 mol of methanol, 0.2 mol of iso-ADT was added thereto, and the mixture was heated at 80°C on a water-bath. The methyl acetate obtained was distilled off with methanol as an azeotropic mixture. After the reaction, the product was distilled to obtain 0.19 mol of iso-dodecatrienol boiling at 96°–98°C/2 mmHg.

Into an autoclave having an inner volume of 100 c.c, 45 g of the iso-dodecatrienol and 1.8 g of nickel-diatomaceous earth (Ni-content: 43%) as a catalyst were added and made to react with shaking under a hydrogen pressure of 50 atms., at 100°–110°C for 2 hours and then at 130°C for 3 hours and further at 150°C for 6 hours. After the reaction was complete, the catalyst was separated by filtration and the filtrate was distilled to obtain 43g of iso-dodecanol (iso-lauryl alcohol,

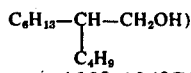

boiling at 122°–124°C/8 mmHg.

The n-ADT was similarly subjected to methanolysis to produce n-dodecatrienol boiling at 101°–103°C/2 mmHg which was further hydrogenated to obtain n-dodecanol (n-lauryl acohol) boiling at 134°–134°C/2 mmHg as also described in the above.

3. Sulfation and Ethoxysulfation of Dodecanol. The iso-dodecanol and n-dodecanol which were obtained in (2) were sulfated by using 1.10 mol of chlorosulfonic acid per mol of dedecanol at 30°C and was neutralized by caustic soda to produce sodium lauryl sulfate. On the other hand, the iso-dodecanol and n-dodecanol were allowed to react with ethylene oxide at 175° ± 2°C in the presence of sodium hydroxide as a catalyst and further sulfated and neutralized as above to produce sodium ethoxylated-lauryl sulfate.

B. Surfactant Properties of Sodium Lauryl Sulfate and Sodium Ethoxylated-lauryl Sulfate The following tests were carried out to examine the surfactant properties as to sodium n-lauryl sulfate (n-$C_{12}OSO_3Na$), sodium iso-lauryl sulfate (l-$C_{12}OSO_3Na$), sodium ethoxylated-n-lauryl sulfate (n-$C_{12}O(EO)_3SO_3Na$) and sodium ethoxylated-iso-lauryl sulfate (i-$C_{12}O(EO)_3SO_3Na$) obtained by the process of (A). In order to compare their surfactant properties, sodium lauryl sulfate (k-$C_{12}OSO_3Na$) and sodium ethoxylated-lauryl sulfate (k-$C_{12}O(EO)_3SO_3Na$) prepared according to the process of (A)-(3), by employing n-lauryl alcohol on the market (a product of Kao Soap Co., Ltd., trade name: Kalchol 20, made from coconut oil) were tested similarly.

1. General Surfactant Properties

As general surfactant properties, (a) surface tension, (b) permeability and (c) foamability were measured using 0.2% and 0.1% aqueous solution of sodium lauryl sulfate and sodium ethoxylated-lauryl sulfate prepared by the foregoing processes. The methods for measuring were as follows:

a. Surface Tension
"Wilhelmy method"
Wilhelmy, L., Ann. Physik 199 186 (1863)

b. Permeability
"Felt Disk Settling method" (modification of canvas disk method, Seyferth, H., et al., American Dyestuff Reptr. 27 527–532 (1938)) S. Hayaski, et al., Yukagaku 6 208 (1957)

c. Foamability
"Ross-Miles method" Oil and Soap, 18 99 (1941)

The results are shown in Tables 1-3.

Table 1

| | Surface Tension (dyn/cm) | | | |
| | Concentration | | | |
| | 0.2 wt% | | 0.1 wt% | |
| | Temperature | | | |
| Sample | 40°C | 25°C | 40°C | 25°C |
|---|---|---|---|---|
| n-$C_{12}OSO_3Na$ | 30.7 | 26.9 | 39.4 | 31.7 |
| i-$C_{12}OSO_3Na$ | 42.0 | 40.4 | 47.4 | 46.3 |
| k-$C_{12}OSO_3Na$ | 39.6 | 40.4 | 39.0 | 38.7 |
| n-$C_{12}O(EO)_3SO_3Na$ | 41.0 | 41.5 | 40.0 | 41.0 |
| i-$C_{12}O(EO)_3SO_3Na$ | 35.4 | 34.1 | 36.2 | 36.5 |
| k-$C_{12}O(EO)_3SO_3Na$ | 38.9 | 40.0 | 36.2 | 40.0 |

Table 2

| | Permeability (sec.) | | | |
| | Concentration | | | |
| | 0.2 wt% | | 0.1 wt% | |
| | Temperature | | | |
| Sample | 40°C | 25°C | 40°C | 25°C |
|---|---|---|---|---|
| n-$C_{12}OSO_3Na$ | 11.0 | 44.3 | 65.8 | 74.0 |
| i-$C_{12}OSO_3Na$ | 41.0 | 116.8 | 183.7 | <300 |
| k-$C_{12}OSO_3Na$ | 15.0 | 47.5 | 22.5 | 73.8 |
| n-$C_{12}O(EO)_3SO_3Na$ | 16.8 | 53.3 | 26.8 | 74.5 |
| i-$C_{12}O(EO)_3SO_3Na$ | 9.8 | 20.8 | 27.5 | 76.5 |
| k-$C_{12}O(EO)_3SO_3Na$ | 12.0 | 28.0 | 20.3 | 53.3 |

Table 3

| | Foamability* (cm) | | | |
| | Concentration | | | |
| | 0.2 wt% | | 0.1 wt% | |
| | Temperature | | | |
| Sample | 40°C | 25°C | 40°C | 25°C |
|---|---|---|---|---|
| n-$C_{12}OSO_3Na$ | 19.3(17.3) | 19.8(17.5) | 18.8(16.7) | 19.0(16.8) |
| i-$C_{12}OSO_3Na$ | 18.0( 4.5) | 16.8( 1.9) | 12.7( 0.6) | 12.3( 0.8) |
| k-$C_{12}OSO_3Na$ | 20.5(17.8) | 20.5(13.3) | 19.0(17.0) | 18.0(16.8) |
| n-$C_{12}O(EO)_3SO_3Na$ | 20.3(17.8) | 19.0(16.3) | 18.5(16.7) | 17.3(15.3) |
| i-$C_{12}O(EO)_3SO_3Na$ | 21.0( 5.7) | 19.8( 2.7) | 17.0( 2.5) | 17.5( 5.3) |
| k-$C_{12}O(EO)_3SO_3Na$ | 21.0(19.0) | 19.3(17.1) | 19.3(18.7) | 18.0(16.0) |

*the height of foam after 5 minutes from the start of measuring.

2. Detergency

Detergency was measured according to the temporary method of the Japan Oil Chemists' Society.

The test cloths and washing conditions were as follows:

| Test Cloth | |
|---|---|
| raw cloth: | muslin R-100 (product of Daito Woolen Spinning & Weaving Co., Ltd.) |
| soil: | beef tallow 2g |
| | fluid paraffin 6g |
| | carbon black 0.42g |
| | carbon tetrachloride 1600g |
| size: | 5 cm × 10 cm (5 pieces) |
| index of reflection of soiled cloth: | 31% |

| Washing Condition | |
|---|---|
| tester: | Laund-O-Meter type |
| concentration | |

-continued

| | |
|---|---|
| of a washing liquid: | 0.1 wt% |
| washing temperature: | 20°C, 40°C |
| amount of washing liquid: | 100cc |
| washing time: | 30 minutes |
| rubber ball: | 5 |
| rinse time: | 5 minutes (twice) |

The solid cloths were washed under the above conditions, air-dried and ironed, and then index of reflection was measured using photovolt type photoelectric reflectometer. The efficiency of washing (D%) was calculated from the average of 5 cloths in accordance with the following formula:

$$D = (R_w - R_s)/(R_o - R_s)$$

wherein $R_o$ is the reflective index of the test cloth before soiling, $R_s$ is the reflective index of the soiled cloth, and $R_w$ is the reflective index of the test cloth after washing.

The results are shown in Table 4.

Table 4

| | Detergency (D%) Temperature | |
|---|---|---|
| Sample | at 20°C | at 40°C |
| n-$C_{12}OSO_3Na$ | 40.0 | 46.5 |
| i-$C_{12}OSO_3Na$ | 38.0 | 42.0 |
| k-$C_{12}OSO_3Na$ | 49.5 | 43.5 |
| n-$C_{12}O(EO)_3SO_3Na$ | 31.0 | 46.5 |
| i-$C_{12}O(EO)_3SO_3Na$ | 26.5 | 45.5 |
| k-$C_{12}O(EO)_3SO_3Na$ | 41.0 | 47.5 |

3. Solubility

1% and 2% aqueous solutions of the samples were charged into a test tube and gradually cooled while stirring the solutions by moving a ring-equipped stirring rod up and down in the tube. The temperature at which the solution became cloudy was measured.

The results are shown in Table 5.

Table 5

| | Clouding Point (°C) Concentration | |
|---|---|---|
| Sample | 20% | 1% |
| n-$C_{12}OSO_3Na$ | 13.5 | 4.0 |
| i-$C_{12}OSO_3Na$ | 11.5 | <0 |
| k-$C_{12}OSO_3Na$ | 18.5 | 6.5 |
| n-$C_{12}O(EO)_3SO_3Na$ | <0 | <0 |
| i-$C_{12}O(EO)_3SO_3Na$ | <0 | <0 |
| k-$C_{12}O(EO)_3SO_3Na$ | <0 | <0 |

4. Foamability Resistance to Oil

The effects of the oil in the washing liquid to the foamability of the surfactant were measured according to "Weeks method" (J.A.O.C.S, 31 254 (1954)). 200 ml of 0.1% aqueous solution of the sample was charged into a graduated mixer and a solution was stirred at high speed for 3 minutes and left to stand for 30 seconds and the height of foam was measured. Then, a certain amount of olive oil was added to the solution and the same operations as above were repeated and the height of foam was measured.

The results are shown in Tables 6 and 7

Table 6

| Amount of Oil (ml.) | Height of Foam (cm) | | | | | |
|---|---|---|---|---|---|---|
| | 0 | 1 | 2 | 4 | 7 | 10 |
| Sample | | | | | | |
| n-$C_{12}OSO_3Na$ | 17 | 17 | 17 | 16.5 | 15 | 14 |
| i-$C_{12}OSO_3Na$ | 16 | 15.5 | 15.5 | 15.7 | 15 | 14 |
| k-$C_{12}OSO_3Na$ | 18 | | | 18 | | 18 |

Table 7

| Amount of Oil (ml.) | Height of Foam (cm) | | | | | | |
|---|---|---|---|---|---|---|---|
| | 0 | 0.5 | 1 | 2 | 4 | 7 | 10 |
| Sample | | | | | | | |
| n-$C_{12}O(EO)_3SO_3Na$ | 15.5 | 16.5 | 17 | 15 | 14 | 12 | 9.5 |
| i-$C_{12}O(EO)_3SO_3Na$ | 12.3 | 11.3 | 10.7 | 10.2 | 8.5 | 6 | 5.2 |
| k-$C_{12}O(EO)_3SO_3Na$ | 15 | 13.7 | 13 | 12.5 | 11 | 9.5 | 5.5 |

The surfactant properties of sodium lauryl sulfate and sodium ethoxylated-lauryl sulfate produced from n-lauryl alcohol which is a derivative of butadiene trimer compare very favorably with those of sodium lauryl sulfate and sodium ethoxylated-lauryl sulfate produced from natural lauryl alcohol. On the other hand, surfactant properties of sodium iso-lauryl sulfate are inferior to those of others. Sodium ethoxylated-iso-lauryl sulfate might be used equally to sodium ethoxylated-lauryl sulfate produced from natural alcohol. Products from iso-lauryl alcohol have foam breaking characteristic. Therefore, it is expected to be used as industrial surfactant such as fiber treating agent (to remove fat from fiber).

We claim:

1. A method for the production of an alkapolyenyl group containing ester in which one molecule of a 1,3-conjugated diene bond containing compound is linked to an alkadienyl group of said ester and which has at least 12 carbon atoms and at least 3 carbon-carbon double bonds, characterized in that an alkadienyl ester represented by the formula $$R\overset{O}{\overset{\|}{C}}O-CH_2-\overset{R_1}{\underset{|}{C}}=\overset{R_1}{\underset{|}{C}}-CH_2-CH_2-\overset{R_1}{\underset{|}{C}}H-\overset{R_1}{\underset{|}{C}}=CH_2$$

in which R is methyl, ethyl, propyl or phenyl and each $R_1$ is independently selected from the group consisting of hydrogen and methyl, is reacted in the presence of a rhodium compound catalyst selected from the group consisting of rhodium chloride, rhodium bromide, rhodium nitrate, rhodium acetate, rhodium propionate, rhodium acetylacetonate, $\pi$- allyl - rhodium chloride, tetrakis(ethylene)dischlorodirhodium and bis(cyclooc-ta-1,5-diene)dichlorodirhodium, with a 1,3-conjugated diene bond containing compound selected from the group consisting of 1,3-butadiene, isoprene and straight-chain dimers thereof, the reaction being conducted at a temperature in the range of 50°–250°C.

2. The method according to claim 1 in which the alkadienyl ester is 1-acyloxy-2,7-octadiene, and the 1,3-conjugated diene bond containing compound is 1,3-butadiene.

3. The method according to claim 1 in which the alkadienyl ester is 1-acyloxy-2,7-octadiene, and the 1,3-conjugated diene bond containing compound is isoprene.

4. The method according to claim 1 in which the alkadienyl ester is 1-acyloxy-2,7-octadiene, and the 1,3-conjugated diene bond containing compound is 1,3,7-octatriene.

5. The method according to claim 1 in which the alkadienyl ester is 1-acetoxy-2,7-octadiene.

6. The method according to claim 1 in which the rhodium compound is an organic acid salt of rhodium.

7. The method according to claim 1 in which the rhodium compound is a rhodium complex.

8. The method according to claim 1 in which the rhodium compound is an inorganic acid salt of rhodium.

9. The method according to claim 8 in which the inorganic acid salt of rhodium is rhodium chloride or rhodium bromide.

10. A method for the production of acetoxy-dodecatriene, characterized in reacting 1,3-butadiene with 1-acetoxy-2,7-octadiene in the presence of a rhodium chloride catalyst at 50°–250°C.

11. 1-acetoxy-2(2-butenyl)-3,7-octadiene.

12. 1-acetoxy-2-(2-butenyl)-2,7-octadiene.

* * * * *